United States Patent [19]

Clark et al.

[11] 4,024,522
[45] May 17, 1977

[54] ACOUSTIC EMISSION SYSTEM FOR WELDING FLAW DETECTION

[75] Inventors: Robert N. Clark, Schaumburg; David W. Prine, Maywood; Fay K. Chin, Lincolnwood, all of Ill.

[73] Assignee: Gard, Inc., Niles, Ill.

[22] Filed: Mar. 15, 1976

[21] Appl. No.: 666,678

[52] U.S. Cl. .............................. 340/248 W; 73/69; 310/8.1; 228/1 R
[51] Int. Cl.² ................. G08B 21/00; G01N 29/04
[58] Field of Search ............... 340/248 W, 253 W; 228/1 R; 73/69; 310/8.1, 8.7

[56] References Cited

UNITED STATES PATENTS

| | | | |
|---|---|---|---|
| 3,191,441 | 6/1965 | Erickson | 340/248 W |
| 3,212,695 | 10/1965 | MacGregor | 228/1 |
| 3,302,277 | 2/1967 | Pruden et al. | 228/1 X |
| 3,406,272 | 10/1968 | Ehrlich | 340/248 W UX |
| 3,573,781 | 4/1971 | Shoh | 340/248 W |
| 3,708,648 | 1/1973 | Croucher et al. | 340/248 W UX |
| 3,784,079 | 1/1974 | Spanjer | 228/1 |
| 3,815,812 | 6/1974 | Tauern | 340/248 W X |
| 3,827,619 | 8/1974 | Cusick et al. | 228/1 |

Primary Examiner—John W. Caldwell
Assistant Examiner—Daniel Myer
Attorney, Agent, or Firm—Claron N. White

[57] ABSTRACT

A system for flaw detection during a continuous welding process uses a transducer to provide a signal burst for each acoustic burst from an article being welded. The signal burst is amplified and filtered to pass frequencies between about 100 and about 550 KHz. The ring-down counter counts signals of the filtered signal burst. The first signal of the filtered signal burst initiates a timing circuit that times out to provide a reset pulse to reset the ring-down counter. If the decimal count exceeds 100 but does not exceed 1000, the ring-down counter operates circuitry to provide a latched signal to an output of a flip-flop to enable a gate before the counter is reset by the reset pulse of the timing circuit. That reset pulse is also provided to the gate to provide at its output a pulse representing one filtered signal burst having more than 100 and no more than 1000 signals during the timing operation. The pulses from the gate are inputs to a pulse counter in the counter mode and a retriggerable monostable multivibrator that, if not retriggered by the next pulse before a predetermined time, resets another flip-flop and resets the pulse counter. If the pulse counter counts a predetermined number of pulses before it is reset, it sets that another flip-flop to provide a signal to an alarm device that turns on a light indicating that there is a weld flaw.

12 Claims, 4 Drawing Figures

ACOUSTIC EMISSION SYSTEM FOR WELDING FLAW DETECTION

BACKGROUND OF THE INVENTION

1. Field of the Invention

There are many nondestructive testing methods, including radiography, dye-check and ultrasonic testing, that are used to examine completed welds.

The present invention relates to the use of acoustic emission to detect flaw formation in welds during welding and cooling phases.

2. Description of the Prior Art

A book entitled, "Research Techniques and Nondestructive Testing" edited by R. S. Sharpe and published in 1970 by Academic Press Inc. (London) Ltd., London, England, includes, as Chapter 1, an article entitled, "Acoustic Emission," that summarizes the state of the art of using acoustic emission to detect and locate flaw growth in pressure containers undergoing hydrostatic testing. It also states that acoustic emission technology has been developed to detect flaw formation in welds during welding and cooling phases and in this regard refers to reports by C. K. Day and W. D. Jolly, that were issued in 1968 as reports BNWL-902 and BNWL-817, respectively. Chapter 1 of the book does not indicate the construction of the system used by Day or Jolly.

Dunegan Research Corporation (now known as Dunegan/Endevco Corp.) had prior to the present invention, a 3000 series acoustic emission instrumentation system that is constructed to provide for research a number of types of instrument evaluation utilizing acoustic emission. In the instruction manual it states that the totalizer of the system can be used to monitor welds. The system discloses preamplification of signals from a transducer, band pass filtering of the preamplified signals, and post-amplification followed by digital counting after signal conditioning. The digital counting is controlled by a digital reset clock. The digital counting uses a ring-down counting method to measure the energy of acoustic emission pulses. The method of ring-down counting used a non-synchronous time interval during which counting occurs. Because it is possible for an acoustic emission pulse to occur over two counting periods, the count in either period may be indistinguishable from lower energy pulses occurring entirely within the counting period. If the counting period is extended so that the probability of splitting pulses over two periods is reduced, the probability of allowing two pulses within the same period is increased. Optimization is possible, but the probability of counting a pulse correctly is limited to less than 100%. In the case of acoutic weld monitoring this maximum probability is about 80% with standard equipment providing ring-down counting.

SUMMARY OF THE INVENTION

The system of the present invention is an acoustic system for welding flaw detection during a continuous welding process. The system is based on the fact that, when a material undergoes stress, several energy release mechanisms come into play. One energy release mechanism is the release of acoustic energy. Others have shown that useful information can be obtained with respect to a stress specimen by monitoring and processing, electrically, the acoustic emission, while the stress is being applied.

The welding of metals produces a unique situation, whereby stress is generated within the weld due to thermal effect as the weld bead solidifies and cools; thus acoustic energy is emitted from a weld as it cools without the need for applying any external source of stress. As early as 1968, Jolly showed, as referred to above, that acoustic emission couled be used to detect flaws in welds during fabrication.

The acoustic emission generated by a weld in the process of formation includes microscopic sources such as dislocation unpinning, phase transformation, and micro-crack formations as well as macro-cracking noise. In addition to these sources of sound from within the weld, the arc, itself, produces acoustical, as well as electrical, noise. If the welding process makes use of a solid flux such as submerged arc or stick welding, the flux cracks as it cools; and this is yet another source of acoustic emission from the welding process. The basic problem of detecting flaws in welds with acoustic emission during the welding process is to provide a system that sorts the multitude of different acoustic signals so as to examine the desired (e.g., flaw) signals while rejecting the many background acoustic signals. This sorting is further complicated in an industrial on-line application by the introduction of extraneous noises such as grinding, hammering, and manipulating the object upon which the weld is being made.

Acoustic emission weld monitoring is an in-process, real-time inspection technique which detects flaws as they are made, not after the fact as in conventional NDT methods. This aspect of acoustic emission is particularly useful in thick multi-pass welds since the possibility exists for achieving repair of faulted early passes before these faults are buried deeply in the weld by subsequent passes. The real-time feature also provides the welder with an immediate warning of welding conditions which are producing flaws, thus allowing him to adjust his parameters and possibly produce less flaws than would normally be produced.

As mentioned above, there is acoustic emission that is generated by the solidification of liquid metal in a cooling weld. Most of the energy is released in the form of individual discrete shock waves, i.e., events, in which the greatest concentration of energy is in the ultrasonic region. Because the shock waves occur at very rapid rates and are apparently random in time, distribution and amplitude, they appear similar to the "noise" that is produced, e.g., in an electric arc. However, the noise of an electric arc is due to minute fluctuations arc in the current and thus differs from acoustic emission noise. Most ultrasonic signals occur primarily from the cooling weld and thus most of the acoustic signals represent a change in the molecular structure of the metal.

The system of the invention provides circuitry to process the electrical signals coming from the transducer, used to listen to ultrasonic signals from the cooling weld, to reject certain electrical signals and pass only electrical signals, that are used to provide a signal that operates an alarm, if there is a flaw in the weld.

The first sorting process provided by the system of the invention is attained by the use of circuitry that limits the frequency spectrum of the electrical signal to be provided to the circuitry used for the second sorting process. The circuitry for the first sorting process includes a band pass filter that passes the portion of the spectrum of the electrical signal containing the greatest amount of energy relevant to the energy resulting from an acoustical emission, as an event, due to the presence of a flaw. To limit the frequency spectrum for subsequent sorting the band pass filter passes frequencies between about 100 KHz and about 400 KHz.

The second sorting process is provided by circuitry that processes the filtered signal from each individual event to determine the amplitude that represents the logarithm of the energy of the event providing the acoustic emission. In this part of the circuitry of the system of the invention the second sorting process provides a ringdown counting of each signal burst passed by the circuitry of the first sorting process. In the system of the invention the ring-down counting differs from the system of ring-down counting, used by others prior to this invention, in that the circuitry synchronizes the start of the counting period with the start of the operation of the ring-down counter to count signals of a signal burst.

In the prior system, illustrated by the use of selected components of the Dunegan/Endevco acoustics emission instrumentation 3000 series mentioned above, the simplified signal burst is an input to a threshold detector that converts input signals to digital pulses for counting purposes. The threshold detector is fixed so as to require a one-volt peak signal before becoming activated. The ring-down counter is reset by a reset clock that periodically provides reset pulses to the counter. After the counter is reset it will count these pulses from the threshold detector until the counter receives the next reset pulse. These pulses that are counted between reset pulses include those of a signal burst that are at least a one-volt peak signal. As the signal burst decreases in amplitude with time, a point is reached at which counting of pulses from a signal burst ceases. In the event that the counter does not receive a reset pulse before the counter receives signals of the next signal burst the counter will count these pulses from the threshold detector until there is a reset signal. Thus the count will not indicate the characteristic of one signal burst so that the reliability of the information is impaired.

The system of the present invention modifies the circuitry of the prior system so that the reset clock is initiated in its predetermined timing operation by the first signal of each signal burst and the reset clock provides, at the completion of its timing period, a reset signal to reset itself to start another timing period when initiated by the first signal of a subsequent signal burst. At the end of that predetermined timing operation of the clock, the reset signal is used to reset the ring-down counter and to reset other components of the circuitry. Because the system of the present invention provides a reliable time period to process one signal burst at a time, the system is not required to use a threshold detector between the input of the ring-down counter and the output of the band pass filter.

The output of the ring-down counter at the end of each predetermined timing period has a decimal count that is used by other circuitry of the second sorting process to provide an output signal, when the reset clock provides the reset signal to that circuitry, if the decimal count is greater than 100 and no more than 1000.

For the third sorting process, the circuitry of the system of the invention includes circuitry that is operative to process the output signals of the circuitry of the second sorting process so as to provide a signal, if there is a predetermined minimum rate of occurrence of events, i.e., acoustic emissions providing for each acoustic emission a signal burst in the system, and if there is a predetermined number of events in a group meeting the predetermined minimum rate of occurrence. In other words, the circuitry requires that the events occur within a predetermined period of time of each other and that the number of events meeting that test constitute a predetermined number for the circuitry of the third sorting process to be operative to provide a signal to alarm means that when thus signalled operate an alarm indicator means that signals the persons of a flaw in the weld.

A fourth sorting process is used in a modification of the system described above. Its use with the other sorting processes is especially preferred. This fourth sorting process is provided by circuitry that functions in accordance with the spectral content of events, and the shape of the event shock wave, modified by attenuation in the sample. The circuitry of the fourth sorting process receives the same signal burst that is received by the ring-down counter. If the signal burst has a particular spectral content of the event, the circuitry of the fourth sorting process provides a signal to the circuitry of the second sorting process. The construction of the circuitry of the second sorting process, in this case, is such that it is operative to provide an output signal to the circuitry of the third sorting process only if a signal is obtained from the circuitry of the fourth sorting process.

The transducer of the invention preferably is a piezoelectric ultrasonic transducer. In a transducer of this type, acoustic emission events excite the fundamental resonance of the transducer, and may also excite the higher harmonics (over-tones) of the transducer, depending on the spectral content of the acoustic emission event. It has been found that some acoustic emission events (e.g., those associated with faulty welds) have an "impulse" shape in which th leading edge of the observed transducer output has a "sharper" edge, and the spectral distribution includes greater high frequency content than other events (e.g., those not associated with faulty welds). Since the first type of acoustic emission event (faulty weld) has greater high frequency content, it tends to excite the higher harmonics (over-tones) of the transducer.

In view of the foregoing, the circuitry of the fourth sorting process includes two filters to separate the fundamental resonance frequency of the transducer from the higher harmonic frequencies. Low and high pass filters are used, with the cutoff of each designed to fall between the fundamental resonance and first overtone. The output of each filter is detected, and peak value determined. These are compared, and an output is generated if the high frequency content is above a certain percentage of the low frequency content.

More particularly with respect to the system of the invention that has been described above, the system comprises: a receiver transducer means, mounted in use on one of the two articles to be welded together; amplifier means to receive a signal burst for each acoustic signal received by the transducer means; ring-down counter means including a binary counter having first and second outputs providing signals when the decimal count exceeds 100 and 1000, the count being approximately proportional to the log of the energy of the acoustic burst to the transducer; clock means that is initiated for its timing operation by the first signal of a signal burst to the binary counter and that, after a predetermined period of time of operation, provides a resetting of the clock means and provides at its output a pulse to reset the ring-down counter means; level discrimination means connected to the output of the clock means and to the first output of the ring-down counter means to provide a signal if there is a signal at the first output of the ring-down counter means during the period of time preceding the pulse at the output of the clock means; output gating means connected to the output of the clock means to reset the gating means and to provide a pulse at the output of the gating means for each signal burst if there is a signal from the level discrimination means and if there is no signal from the second output of the ring-down counter means indicating a decimal count of the amplitude of the signal burst exceeding a first predetermined count and a second predetermined higher count, respectively, e.g., greater than 100 and no more than 1000, respectively; rate detector means connected to the output gating means to provide a signal at its first output in response to a pulse at its input, that continues only if the subsequent pulses are each received from the output gating means within a predetermined period of time subsequent to the preceding pulse from the output gating means and to provide a pulse at the second output of the rate detector means after the signal at the first output; pulse counter means connected to the output gating means to count pulses, said pulse counter means being connected to the second output of the rate detector means to be reset by the pulse at that second output; alarm means having a first input, that is connected to the first output of the rate detector means, and a second input that is connected to the output of the pulse counter means, to provide a signal when the pulse counter means counts at least a predetermined minimum number of pulses; alarm indicator means connected to the output of the alarm means to operate by a signal from the alarm means. When the signal at the first output of the rate detector means ceases, the alarm means is operated to cease the signal at its output, if that signal was initiated by a signal to the first input of the alarm means from the pulse counter means.

Preferably, the system further includes: a high-pass filter and a low-pass filter connected to the amplifier means; first and second detectors connected to the output of the high-pass filter and low-pass filter, respectively, to provide from each a voltage, indicative of the peak value of the output of the filters; comparator means connected to the outputs of the first and second detectors to provide, for each signal burst, an output signal, only when the ratio of these input voltages exceeds a predetermined value, said output of the comparator means being connected to an input of the output gating means that is constructed to require this output signal from the comparator means in order to provide a pulse, when the output gating means receives a reset signal from the clock means, to the rate detector and pulse counter means.

To prevent the passage of undesirable external signals, such as radio signals, to the input of the ring-down counter means the system includes band pass filter means, between the amplifier output and the input of the ring-down counter, to pass frequencies between about 100 KHz and about a frequency that effectively prevents passage of these undesirable external signals having higher frequencies. The band pass filter means preferably is one that passes frequencies up to about 550 KHz and it is especially preferred that the upper frequency is about 400 KHz.

DETAILED DESCRIPTION

Figure 1:
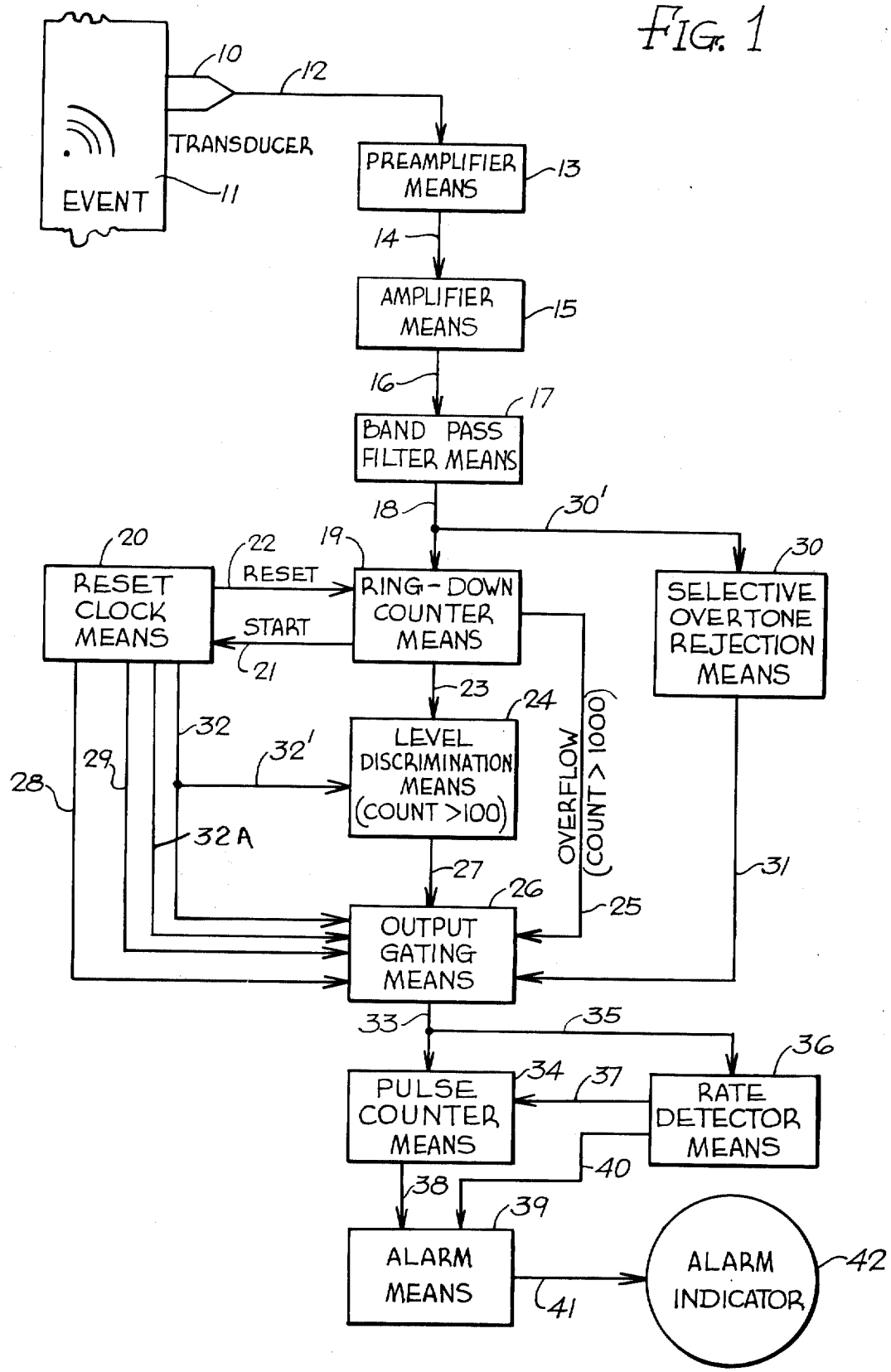
FIG. 1 is a block diagram of the preferred embodiment of the system of the invention including the selective overtone rejection means that provides the fourth sorting process mentioned above.

As seen in FIG. 1, a receiver transducer 10 is mounted on a metal article 11 adjacent the area where the metal article is being welded to another metal article. The flaw in the weld provides an acoustic emission, as an acoustic burst, that is shown schematically as an event in metal article 11. Of course, the event actually occurs in the weld during its cooling.

The metal article 11 can be illustratively a plate or a pipe that is welded to another plate or pipe, respectively. The transducer 10 is preferably a piezoelectric transducer that provides a suitable pickup of acoustic emissions, including those due to flaws, and converts to signal bursts, each within a frequency range, e.g., between about 100 KHz and about 400 KHz, that contains the frequencies due to acoustic emission events from flaws that are received by the transducer.

The output of transducer 10 is connected by a line 12 to a preamplifier means 13 that has its output connected by line 14 to an amplifier means 15. The output of amplifier means 15 is connected by a line 16 to the input of a band pass filter means 17, illustratively passing frequencies between about 100 KHz and about 550 KHz, and preferably between about 100 KHz and about 400 KHz.

The output of band pass filter means 17 is connected by a line 18 to an input of a ring-down counter means 19. A reset clock means 20 has an input connected by a line 21 to ring-down counter means 19 to receive the first signal of a signal burst provided by line 18 to ring-down counter means 19. The reset clock means 20 illustratively includes an oscillator 20A and timing circuitry. The oscillator has its output connected to an input of a NAND gate 20B that has its other input connected to the output of a R-S flip-flop 20C that has its set input connected by line 21 to ring-down counter means 19. The output of the NAND gate 20B is connected to the input of the first decade counter of 3-stage decade counters 20D. The output of the third decade counter is connected to the reset input of the flip-flop 20C via an inverter 20E. The illustrative reset clock means further includes a monostable multivibrator 20F that has its input connected to the output of the flip-flop 20C mentioned above.

The construction of reset clock means 20 with its decade counters 20D, flip-flop 20C and multivibrator 20F is such that the flip-flop 20C is reset by the output of the third decade counter at the completion of its count. When this occurs, the flip-flop 20C no longer enables the gate between the oscillator 20A and the first decade counter. At the same time, this change of the voltage signal at the output of the flip-flop 20C, after a delay, produces pulses at the Q and $\overline{Q}$ outputs of the multivibrator 20F. These pulses constitute reset pulses that are utilized for the purposes described below and collectively referred to as a reset pulse.

Between the flip-flop and the input of the multivibrator 20F is a number of inverters 20G through 20L to provide a delay in the change in the signal between the output of the flip-flop and the input of the multivibrator 20F. A line 28, that is connected to the line connecting inverter 20H inverter 20I, is connected to another component to provide it with a signal for the purpose described later. A line 29 providing a preliminary reset signal is connected to the line connecting the output of inverter 20I to the input of inverter 20J. That signal is used as described later. The frequency of the output of the oscillator is illustratively such that the output signal from the third decade counter occurs about 20 milliseconds after the NAND gate 20B is enabled by the flip-flop 20C and after a further delay, provided by the time to provide output signals from the set of inverters 20G through 20L to provide an input signal to the monostable multivibrator 20F, it provides the reset pulse mentioned above. This pulse to the reset inputs of the decade counters 20D by a line (not numbered) resets them. This construction of the reset clock means 20 is not shown in FIG. 1 except to show that a signal to line 21 starts the counting of reset clock means 20 and that clock means provides, by a line 22 connected to ring-down counter means 19, a pulse that resets the latter. The pulse provided by line 22 is the reset pulse from the monostable multivibrator 20F of clock means 20 that has been described above. The monostable multivibrator 20F provides the reset pulse illustratively about two microseconds after the occurrence of the output signal from the third decade counter. The construction is shown in FIG. 3.

Figure 3:
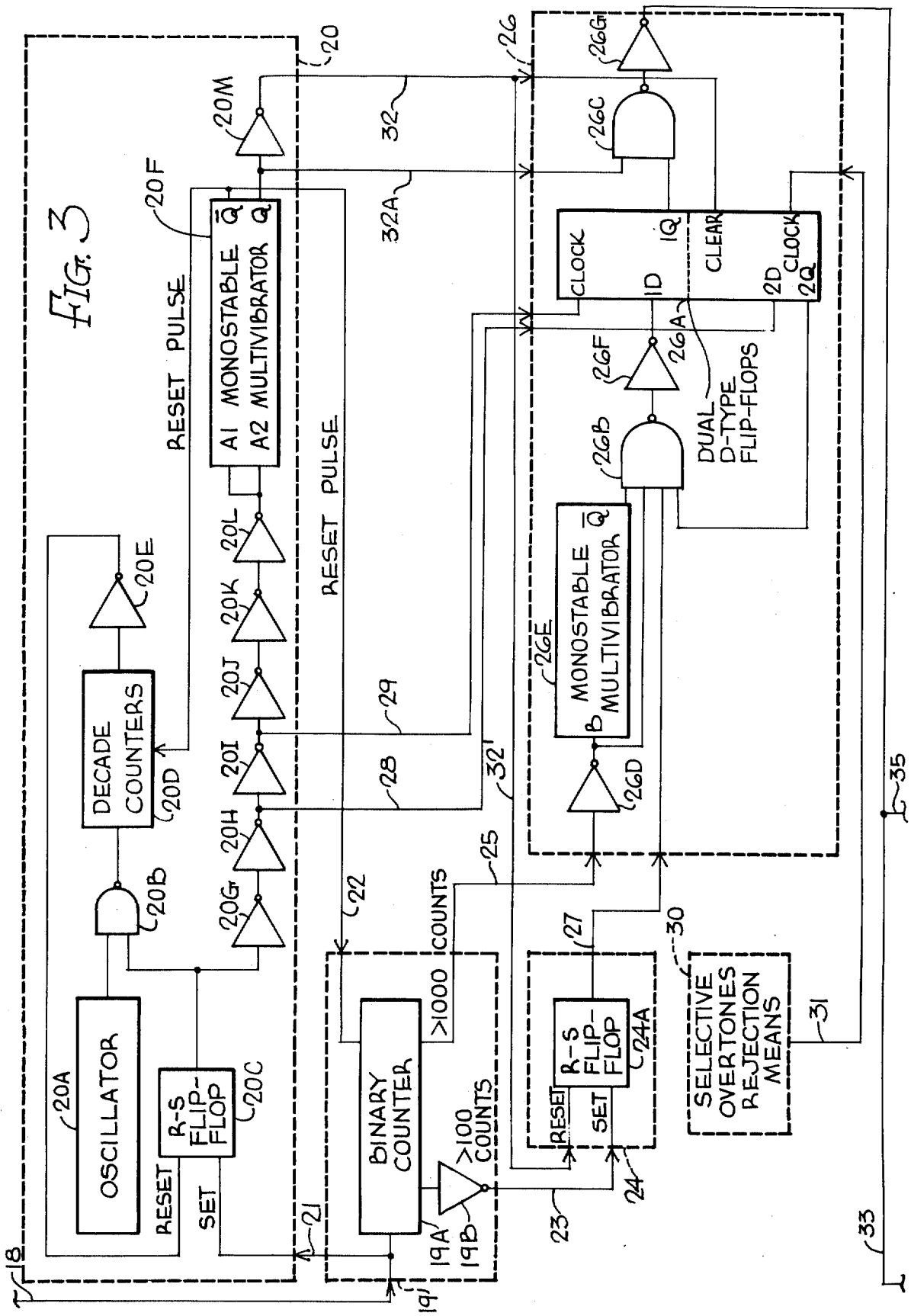
FIGS. 3 and 3A are a schematic electrical drawing showing in greater detail the circuitry of a part of the system of the invention shown in FIG. 1.

The ring-down counter means 19, as shown in FIG. 3, includes a binary counter 19A having a number of outputs, only two of which are used to provide signals to other components of the system. These two outputs are referred to in this application as the first and second outputs. The counter 19A after being reset counts the voltage signals of a voltage burst until the reset input of the counter 19A receives the reset pulse mentioned above. The first output provides a signal when the decimal count exceeds 100. The second output provides a signal when the decimal count exceeds 1000. This signal at the second output is called an overflow signal and really means that the energy due to the acoustic burst to the transducer is higher than the energy due to the acoustic burst from a weld flaw. For this reason this overflow signal is used to inhibit the operation of subsequent sorting processes that would be operative as a result of the signal from the first output. The count is approximately proportional of the log of the energy of the acoustic burst to the transducer that provides the signal burst. The first output is connected to an inverter 19B that has its output connected by a line 23 to a level discrimination means 24. The second output is connected by a line 25 to one input of an output gating means 26 as described below. The output of level discrimination means 24 is connected to another input of output gating means 26 as described below. The level discrimination means 24 illustratively is a R-S flip-flop 24A having a set input and a reset input. The set input is connected to the first output of the binary counter 19A of ring-dow counter means 19 by line 23 and inverter 19B. The output of this flip-flop is connected by a line 27 to output gating means 26.

The output gating means 26, as shown in FIG. 3, illustratively includes dual D-type flp-flops 26A (SN7474), a four-input positive-NAND gate 26B (SN7440), and a two-input positive-NAND gate 26C (SN7400). The line 27 is connected to the first input of the four-input NAND gate 26B of output gating means 26. The line 25 is connected to an inverter 26D that has its output connected to the second input of the four-input NAND gate 26B. The output of inverter 26D is also connected to the B input of another monostable multivibrator 26E (SN74121) that has its $\overline{Q}$ output connected to the third input of the four-input of NAND gate 26B of output gating means 26. This construction of providing the multivibrator between the inverter and the third input, rather than merely connecting the output of the inverter to the third input as well as to the second input of the four-input NAND gate, or rather than providing a continuous positive signal to the third input, is for a useful purpose described below.

In the event that, during the counting of the binary counter, there is a decimal count that is no more than 1000, there is no positive signal at the second output of the binary counter 19A. In this case there is a low signal in line 25 to the inverter 26D so that its output provides a high signal to the second input of the four-input NAND gate 26B of output gating means 26 and provides a high signal to the B input of the monostable multivibrator and thus a high signal from its $\overline{Q}$ output to the third input of that four-input NAND gate 26B. Thus, the high level voltage to the first input of the four-input NAND gate 26B due to the high level signal at the first output of the binary counter will result in the enabling of the four-input NAND gate 26B. Then the gate will provide a low level signal when there is a high level signal provided to the fourth input of that gate from the Q output of the second flip-flop of the dual flip-flop 26B, mentioned above as one of the components of output gating means 26.

However, if the decimal count exceeds 1000 the second output of the binary counter 19A of ring-down counter means 19 provides a high signal that is inverted by the inverter 19B connected to line 25 so that the output of that inverter provides a low signal to the second input of the four-input NAND gate 26B. This prevents the enabling of that gate to change its output when it receives the signal from the Q output of the second flip-flop of the dual flip-flop 26A. This high signal from the second output of the binary counter 19A is a change in the signal to the B input of the monostable multivibrator 26E having its $\overline{Q}$ output connected to the third input of the four-input NAND gate, but this results in no change in the signal at the $\overline{Q}$ output. However, when the binary counter 19A is reset by the reset pulse in line 22 from reset clock means 20, this results in a change in the output signal at the second output of the binary counter 19A. As a result, the input signal to the B input of the monostable multivibrator 26E becomes a high signal. This produces a low pulse at the $\overline{Q}$ output of the monostable multivibrator 26E. The timing of multivibrator 26E is adjusted so that it will provide this low signal to the third input of the four-input NAND gate 26B of output gating means 26 for a period of time equivalent of the several periods of operation of the binary counter 19A of ring-down counter means 19. This insures that the subsequent operation of the binary counter by voltage signals will not provide an enabling of the four-input NAND gate 26B of output gating means 26. This prevents the enabling of output gating means 26 for any subsequent portions of a signal burst, that is due to the transducer coverting an acoustic noise other than occurring as a result of the welding operation.

Line 28 is connected to the D input of the second D-type flip-flop of the dual D-type flip-flops 26A, mentioned above as part of the circuitry of output gating means 26. Line 29 provides a preliminary delay reset pulse to the clock input of the first flip-flop of the dual D-type flip-flops 26A. A line 32 connects the output of the monostable multivibrator 20F via an inverter 20M of reset clock means 20 to the clear input of the second flip-flop of the dual D-type flip-flops 26A of output gating means 26. The reset pulse in line 32 clears that flip-flop.

The line 32 is connected by a line 32' to the reset input of the flip-flop 24A of level discrimination means 24 so that the reset pulse from the inverted reset pulse from the Q ouput of multivibrator 20F of reset clock means 20 resets that flip-flop of level discrimination means 24 via lines 32 and 32' at the time that the reset pulse on line 32 resets the second flip-flop of the dual D-type flip-flops 26A, of output gating means 26 and the noninverted pulse on a line 32A provides a pulse to the two-input NAND gate 26C connected by line 32A directly to the Q output of the first flip-flop of the dual D-type flip-flops 26A so as to provide a pulse counter means 34 and to rate detector means 36. Of course, that pulse in line 33 is provided if the count in counter 19A of ring-down counter means 19 is greater than 100 and no more than 1000 and a signal has been provided by selective overtone rejection means 30 via line 31 to NAND gate 26B of output gating means 26.

The line 28 is connected to the D input of the second flip-flop of the dual D-type flip-flops 26A. When the flip-flop 20C of reset clock means 20 is set to provide a high signal at its output due to the first voltage signal of the voltage burst from transducer 10, line 28 provides a high signal to the D input. During the timing period of the reset clock means 20 the clock input of this second D-type flip-flop of flip-flops 26A will receive a signal from a selective overtone rejection means 30 that has its output connected by a line 31 to that clock input and that has its input connected to line 18 by a line 30'. As a result the Q output of that flip-flop provides a high signal to a line connecting it to the fourth input of the four-input NAND gate 26B. When this high signal is provided to that NAND gate a low signal is passed at its output to the input of an inverter 26F, of output gating means 26, that has its output is connected to the D input of the first D-type flip-flop of flip-flops 26A. This occurs only if the flip-flop 24A of level discrimination means 24 is set by the first output of the digital counter of ring-down counter means 19 and if the second output of the digital counter does not provide a high voltage signal to line 25.

After the D input of the first D-type flip-flop of flip-flops 26A of output gating means 26 receives the high signal from the output of the inverter 26F connected to the four-input NAND gate, the clock input of the first D-type flip-flop of flip-flops 26A receives the preliminary delay reset signal from line 29. Thus, when that clock D input goes high, the Q output of the first D-type flip-flop is latched to a high signal that is provided to one input of the two-input NAND gate 26C, mentioned above as a component of output gating means 26. This signal enables that two-input NAND gate 26C, so that, when it receives the reset pulse from line 32A, a low voltage pulse is provided by that gate to another inverter 26G, that is another component of output gating means 26. The output of inverter 26G is connected by a line 33 to pulse counter means 34. A line 35 is connected to line 33 and to a rate detector means 36.

When the reset pulse is provided to the clear input of the second D-type flip-flop by line 32, the Q output of that flip-flop changes to a low signal. Thus the output of four-input NAND gate 26B changes to a high signal. This changes the signal to the D input of the first D-type flip-flop of the dual flip-flops 26A to a low signal but this does not change the signal provided by the Q output of the first D-type flip-flop of flip-flops 26A until there is a high reset signal at its clock input as a result of the operation of counters 20D initiated by the first signal of the next voltage burst from transducer 10 and following a high signal at the D input of that flip-flop resulting from that voltage signal burst.

Figure 3A:
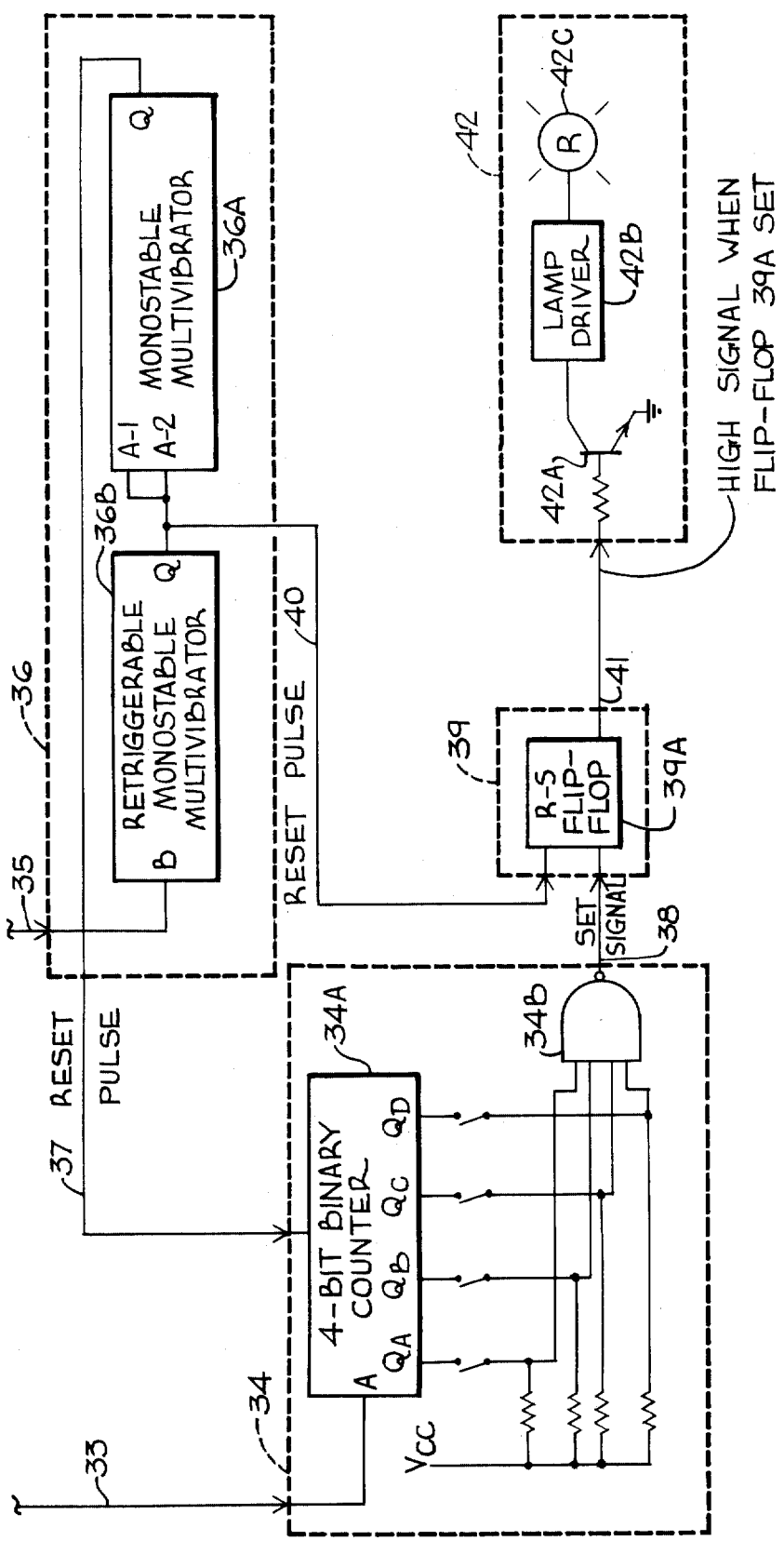

The pulse counter means 34, as seen in FIG. 3A is illustratively a four-bit binary counter 34A (SN7493) that has its A input connected to line 33. The reset input is connected to a line 37 that is connected to the Q output of a monostable multivibrator 36A (SN74121) described below as a component of the illustrative construction of rate detector means 36. The circuitry of pulse counter means 34 includes switches (not numbered) that are connected to the $Q_A$, $Q_B$, $Q_C$, and $Q_D$ outputs of the binary counter 34A to connect these outputs selectively to the inputs of a four-input positive-NAND gate 34B of pulse counter means 34. The switches are closed manually or can be closed automatically by circuitry operated by turning a dial to a position to obtain a specific combination of open and closed switches.

The circuitry of pulse counter means 34 is additionally such that when specific switches are closed the binary counter has those outputs, that are connected to the closed switches, providing a low level signal to the corresponding inputs of the four-input NAND gate 34B of pulse counter means 34 even though each line connecting a switch to an input of the NAND gate is connected to a positive voltage source. This is because the low level signal from a counter output overrides the positive voltage to provide a low level signal to that input of the gate. For each closed switch this overriding occurs until that output of the pulse counter connected to the closed switch is provided a high level signal. As a result, until sufficient pulses have been counted by the pulse counter to provide a high level signal at each of the outputs connected to closed switches, the output of the four-input NAND gate 34B is a high level signal. That output of the four-input NAND gate of pulse counter means 34 is connected by a line 38 to an alarm means 39 that illustratively is a R-S flip-flop 39A. The line 38 is actually connected to the set input of that R-S flip-flop. The reset input of flip-flop 39A of alarm means 39 is connected by line 40 to the Q output of a retriggerable monostable multivibrator 36B (SN74122 of rate detector means 36.

The rate detector means 36 illustratively includes the retriggerable monostable multivibrator 36B and the monostable multivibrator 36A mentioned above. The B input of the retriggerable monostable multivibrator 36B is connected by lines 33 and 35 to the output of inverter 26G of output gating means 26. The Q output of the retriggerable monostable multivibrator is connected by a line (not numbered) to the A1 and A2 inputs of the monostable multivibrator 36A that has its Q output connected to the reset input of the counter 34A of pulse counter means 34 by line 37. The Q output of the retriggerable monostable multivibrator 36B is connected to line 40 that is connected, as described above, to the reset input of the flip-flop of alarm means 39.

The output of the flip-flop 39A of alarm means 39 is connected by a line 41 to an alarm indicator 42 that includes a transistor 42A having its base connected by line 41 to the output of the flip-flop of alarm means 39. The collector of the transistor is connected to a lamp driver 42B to turn on an alarm light 42C while the transistor is conducting. This occurs when there is a high signal in line 41 from the output of the flip-flop 39A of alarm means 39.

Until a pulse is provided from output gating means 26 via lines 33 and 35 to multivibrator 36B by the reset pulse a line 32A, as described above, the Q output of the retriggerable monostable multivibrator 36B provides a low level signal to the reset input of the flip-flop 39A of alarm means 39 and the four-input NAND gate 34B of pulse counter means 34 provides a high level signal to the set input of the flip-flop 39A of alarm means 39. As a result the output of that flip-flop is a low level signal to the transistor of alarm indicator 42. Thus the light 42C of alarm indicator 42 is off. When the first pulse is provided to the B input of the retriggerable monostable multivibrator 36B of rate detector means 36, the Q output of that multivibrator changes to provide a high level signal to the reset input of the flip-flop 39A of alarm means 39. The output of that flip-flop remains a low signal because each input of the four-input NAND gate 34B of pulse counter means 34, that is connected by a closed switch, is provided a low level signal so that there remains a high level signal at the output of the four-input NAND-gate 34B. If the number of pulses counted within the period of operation of the retriggerable monostable multivibrator 36B equals or exceeds the minimum number of pulses required to be counted for the period determined by the operation of rate detector means 36, the outputs of counter 34A of pulse counter means 34 provide high level signal so that the output of the four-input NAND gate 34B is a low level signal. As a result, this low level signal to the set input of the flip-flop 39A of alarm means 39 will change the output of the flip-flop 39A of alarm means 39 to a high level signal. The light 42C is turned on. If this minimum number of counts are not received by the counter 34A of pulse counter means 34 by the time that the Q output of the retriggerable monostable multivibrator 36B changes to a low signal to the reset input of the flip-flop 39A of alarm means 39, the signal will change at the Q output of multivibrator 36B from a high level signal to a low level signal. The flip-flop 39A of alarm means 39 will remain reset. This inhibits a resetting of flip-flop 39A if counter 34 counts another pulse to provide a low level signal on line 38. As a result, the output of that flip-flop still provides a low level signal to the transistor 42A. The light 42C remains unlit.

So long as the retriggerable monostable multivibrator 36B of rate detector means 36 receives a pulse to retrigger it before the normal end of the pulse at the Q output the high level pulse at the Q output continues. The retriggerable monostable multivibrator 36B is constructed to provide an output pulse for a period of time so that it is extended by input pulses that must be provided for each within a predetermined period of time. During the period of the first pulse and any extensions by retriggering there is a number of pulses to the counter 34A of pulse counter means 34. If that number of pulses counted is less than the number, that would be received when the pulses are due to acoustic bursts resulting from a weld flaw, there is no change in line 41 from the output signal of alarm means 39. During cooling of a weld with a flaw, pulses will be generated of a greater amplitude than those from a good weld; the greater pulses could occur an average of about 1/3 second apart and could number about 6–10 pulses in all, depending on weld conditions and geometry.

When the retriggerable monostable multivibrator 36B does not receive a pulse from line 35 to retrigger it within the time required for retriggering, the Q output changes to a low level signal to the reset input of the flip-flop 39A of alarm means 39. When this occurs, the output of that flip-flop will change to provide a low level signal to the transistor 41. This low level signal from the output of the flip-flop of alarm means 39 turns off the light. This resetting of the flip-flop 39A of alarm means 39, by the low level signal from the Q output of the retriggerable monostable multivibrator 36B, occurs if the required minimum count is obtained by the pulse counter 34A, during the period of time that is in a count mode of operation, to provide a low level signal to the set input that resulted in a high level signal from the flip-flop output to the transistor 42A to turn on the light 42C. The other output of flip-flop 39 is connected by a line 41A to the B input of the monostable multivibrator 36A and that output at the same time provides low level signal to that B input while there is a low level signal provided to the transistor 42A.

When the retriggerable monostable multivibrator 36B of rate detector means 36 is no longer retriggered within the required time period, the Q output will shortly change to a low level signal, as described earlier, so that the A1 and A2 inputs of the monostable multivibrator 36B receive a low level signal. As a result, the Q output of that monostable multivibrator provides by line 37 a high level pulse to the pulse counter 34A. This results in a resetting of the counter 34A of pulse counter means 34. At the end of that pulse, the Q output provides the low level signal to the counter 34A so that is is again in the count mode.

Figure 2:
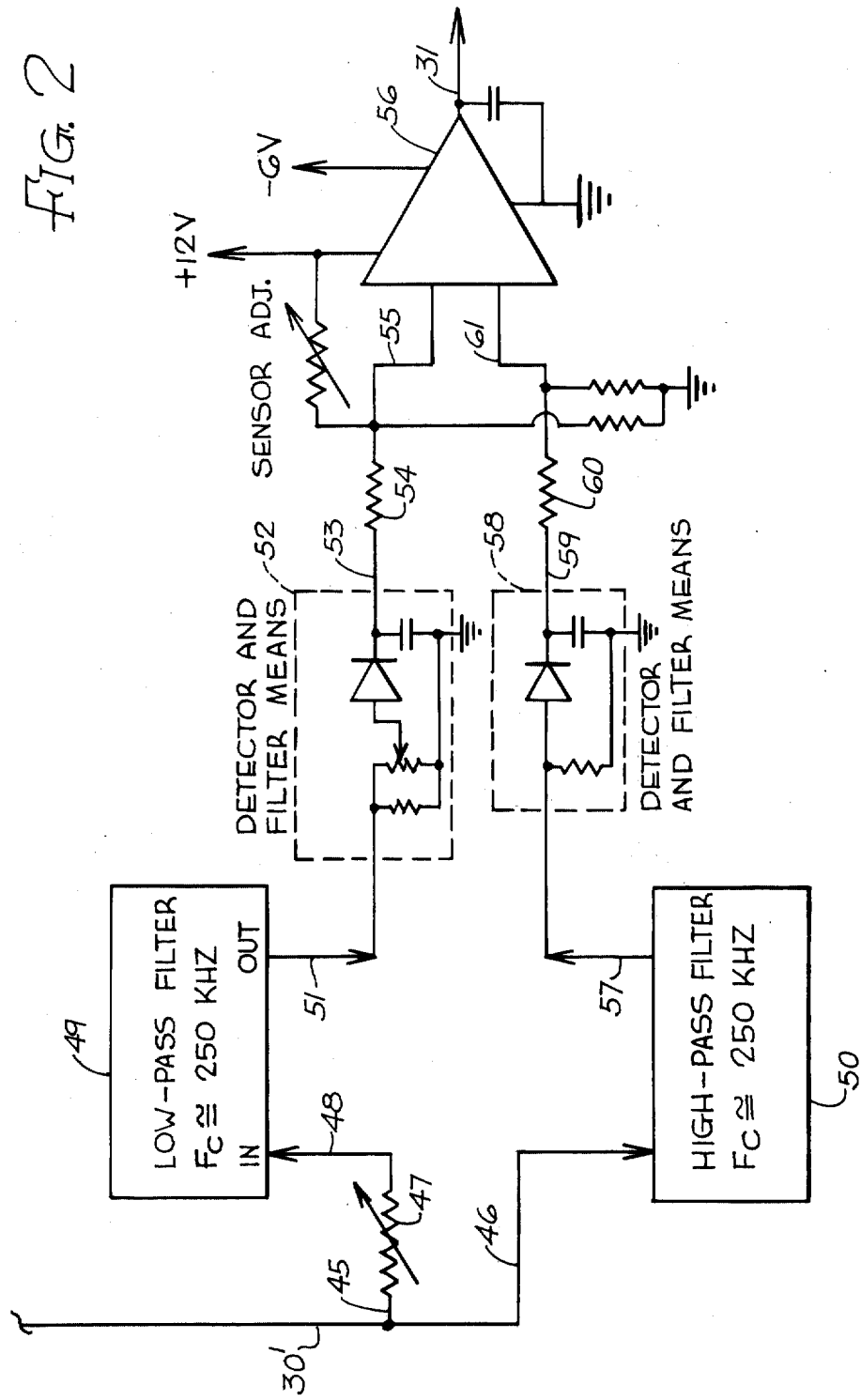
FIG. 2 is a diagram showing some details of construction of the selective overtone rejection means.

Referring to FIG. 2, that shows an illustrative construction for selective overtone rejection means 30, a line 45 and a line 46 are connected to line 30' that is connected by line 18 to band pass filter means 17. The line 45 is connected by variable resistor 47 to a line 48 that is connected to the input of a low-pass filter 49 that passes frequencies up to 250 KHz. The line 46 is connected to the input of a high-pass filter 50 that passes frequencies of at least 250 KHz.

The output of filter 49 is passed by a line 51 to a detector and filter means 52 that has its output connected by a line 53, a resistor 54 and a line 55 to an input of the comparator 56. The output of filter 50 is connected by a line 57 to a detector and filter means 58 that has its output connected by a line 59, a resistor 60 and a line 61 to another input of comparator 56.

The detector and filter means 52 includes a diode (not numbered) connected to a potentiometer (not numbered) connected to line 51 and to ground. The line 51 is also connected by a resistor (not numbered) to ground. The output of the diode is connected to a capacitor (not numbered) that is connected to ground as well as to line 53. The detector and filter means 58 has a diode (not numbered) with its output connected to line 59 and its input connected to line 57 that is connected by a resistor to ground. The output of the diode is connected by a capacitor (not numbered) to ground and to line 59. The output of comparator 56 is connected to line 31. The other connections to lines 55 and 61 and to capacitor 56, that are shown, do not require any explanation.

Each of detector and filter means 52 and 58 converts the AC input signals to a peak-value DC signal. The detector and filter means 52 has its potentiometer adjusted so that when the DC output signal by line 55 to one input of comparator 56 is compared with the DC output signal from detector and filter means 58 via line 61 to the other input of comparator 56, the DC signal in line 61 must be greater than the DC signal in line 55 to provide a high level signal from the output of comparator 56 via line 31 to the clock input of the second D-type flip-flop of dual D-type flip-flops 26A of output gating means 26. This adjustment is such to indicate that the high-frequency content of the signal burst is above a predetermined percentage of the low-frequency content of that signal burst. This requirement is met by signal bursts that are due to acoustic bursts resulting from weld flaws but is not met by signal bursts resulting from other acoustic emissions.

The alarm indicator 42 has been described above as illustratively including a transistor. Instead of a simple npn transistor, alarm indicator 42 can include a silicon control rectifier connected to the output of the flip-flop 39A of alarm means 39 so that the light 42C remains lit when the output signal of that flip-flop changes to a low level signal. In this modification the rectifier is switched off when desired so that the light 42C will be lit the next time a flaw is detected.

The system of the invention can include additional components, as described below, to locate the weld flaw at the time the system operates to turn on the light 42C of alarm indicator 42. In this modification of the system to provide a locating ability, the system includes a second transducer that is mounted on the article on which transducer 10 is mounted. The additional transducer is also located adjacent the zone where the welding occurs, as in the case of transducer 10, but it is located so that the welding zone is between the two transducers. This modification includes additional preamplifier means 13, amplifier means 15, band pass filter means 17, ring-down counter means 19, and level discrimination means 24, that are connected to one another and to the additional transducer, as shown in FIG. 1 for the non-modified system. The additional ring-down counter means and the level discrimination means have the construction described above for ring-down counter means 19 and level discrimination means 24 of FIG. 1. The reset clock means 20 has a second R-S flip-flop and an additional 3-stage decade counter that has an input connected to the line connecting the output of the additional band pass filter means to the input of the additional counter of the additional ring-down counter means. This additional flip-flop of reset clock means 20 has its other input connected to the output of the additional inverter connected to the D output of the third stage counter of the additional three-stage decade counter of reset clock means 20. The output of this additional flip-flop of reset clock means 20 is connected by a second additional inverter to an input of an additional two-input NAND gate that has its other input connected to the oscillator of reset clock means 20. The output of that NAND gate is connected to the input of the first counter of the additional three-stage decade counter of reset clock means 20. In the description of the nonmodified illustrative system it is stated that there is a number of inverters 20G through 20L between the output of the flip-flop 20C of reset clock means 20 and the monostable multivibrator 20F of reset clock means 20. In the modified system the second inverter 20H is replaced by that additional two-input NAND gate and that gate has one input connected by the first inverter 20G to the output of the flip-flop 20C of reset clock means 20 while the other input of the NAND gate is connected to the output of that second additional inverter having its input connected to the output of the additional flip flop. As a result the signal at the output of that additional two-input NAND gate will be inverted whenever either R-S flip-flop is reset by the associated three-stage decade counter completing its period of timing.

The modified system further includes first and second monostable multivibrators (SN74121). The A1 and A2 inputs of the first multivibrator are connected to the output of the flip-flop 20C that has been described as a part of reset clock means 20 for the unmodified system. The A1 and A2 inputs of the second multivibrator are connected to the output of the additional flip-flop. Each of the two multivibrators has its B input connected to the output of the inverter 26F that is connected to the D input of the first D-type flip-flop of dual D-type flip-flops 26A to provide a hold signal to the multivibrators. By this construction each of these first and second additional multivibrators provide pulses to a conventional device that can provide a readout indicating the location of the flaw on the basis of the difference in time between the pulses.

As seen below, the preferred embodiment of the system of the invention, illustrated by certain circuitry for some of the components, has been proved successful to detect a number of weld flaws that have been found, after the welding operation, using the conventional radiography, etc., testing methods for flaws. The initial testing of the system used the system without selective overtone rejection means 30 and thus the circuitry of output gating means 26 was constructed to be operative, without requiring a signal from selective overtone rejection means 30, to provide an output pulse to line 33 when output gating means 26 receives a reset pulse from reset clock means 20.

The system, without the selective overtone rejection means 30, has been used for an in-process weld monitoring of submerged arc welding in the manufacture of carbon steel tanks for railroad tank cars. The results using the system have been compared satisfactorily with an inspection of the completed tanks using conventional nondestructive testing methods, such as radiography, that are still required to meet the ASME Code for adequate welds.

The system of the invention has been used to monitor acoustic emissions in the welding of piping used for nuclear power plants. The results were compared to the standard ASME Code examination results. In the fabrication of nuclear power plant piping there is a wide range of sizes, materials and welding methods. On the basis of the study to date of the system, it is believed that every type of weld process can be monitored to a reasonable degree of reliability to detect weld flaws.

The foregoing description has been presented solely for the purpose of illustration and not by way of limitation of the invention because the latter is limited only by the claims that follow.

We claim:

1. An acoustic emission system for welding flaw detection using a receiver transducer means, mounted in use on one of the two articles to be welded together to receive an acoustic burst from the article on which it is mounted and to provide at its output a signal burst, which comprises:

amplifier means having an input that is connectable to the output of the transducer means and having an output;

ring-down counter means having a first input and a second input, said first input being connected to said output of said amplifier means, and said ring-down counter means including a binary counter having a first output and a second output providing signals when the decimal count of the amplitudes of a signal burst exceeds a first predetermined count and a second predetermined higher count, respectively;

clock means having an output and an input that is connected to said output of said amplifier means, said clock means being constructed to initiate its timing operation in response to said first signal of the signal burst from said amplifier means and that, after a predetermined period of time of operation, provides a resetting of said clock means to be able to start another timing operation for the predetermined period of time when initiated again by said first signal of the next signal burst and provides a pulse at its output, and said output being connected to said second input of said ring-down counter means to provide a reset of its counter by the pulse from said output;

level discrimination means having an output, a first input that is connected to said first output of said counter of said ring-down counter means, and a second input that is connected to said output of said clock means, said level discrimination means being constructed to provide a signal at its output when it receives a pulse from said clock means if said level discrimination means receives a signal from said first output of said counter of said ring-down counter means that is provided when the decimal count is said counter has exceeded the first predetermined count;

output gating means having an output, a first input connected to said output of said level discrimination means, a second input connected to said second output of said counter of said ring-down counter means, and a third input connected to said output of said clock means, said output gating means being constructed to provide a pulse, based on the pulse from said clock means to said output gating means, if the said output gating means is provided a signal from said level discrimination means and if said second output of said counter of said ring-down counter means does not provide the signal that is provided when the decimal count in said counter has exceeded the second predetermined count;

rate detector means having an input and first and second outputs, said rate detector means being constructed to provide a signal at its first output in response to a pulse at its input that continues only if each subsequent pulses are each received at said input of said rate detector means within a predetermined period of time subsequent to the preceding pulse from said output gating means and to provide a pulse at the second output of said rate detector means after the signal at said first output of said rate detector means;

pulse counter means having an output and a first input connected to said output of said output gating means to receive each pulse provided at said output of said output gating means, and a second input connected to said second output of said rate detector means, said pulse counter means being constructed to count pulses received at said first input during the period of time that a pulse is not provided to its second input from said second output of said rate detector means, said pulse from said second output of said rate detector means resetting said pulse counter means, and said pulse counter means further being constructed to provide a signal at its output if the number of counts of pulses, before its reset by the pulse from the second output of said rate detector means, is at least a predetermined minimum number of counts;

alarm means having an output, a first input that is connected to said first output of said rate detector means, and a second input that is connected to said output of said pulse counter means, said alarm means being constructed to provide a signal at its output that is initiated when there is a signal at its second input and that ceases when there is a signal at its first input; and alarm indicator means having an input connected to said output of said alarm means and being operative in response to said signal provided by the said alarm means to indicate a weld flaw.

2. The system of claim 1 wherein the receiver transducer is a piezoelectric transducer, and said first and second outputs of said binary counter of said ring-down counter means provide a signal when the decimal count exceeds 100 and 1000, respectively, said system further including band pass filter means having an input connected to said output of said amplifier means and having an output connected to said input of said ring-down counter means to provide amplified signal bursts from said amplifier means to said ring-down counter means, said band pass filter means being constructed to pass frequencies between about 100 KHz and about 550 KHz.

3. The system of claim 2 wherein said band pass filter means passes frequencies only between about 100 KHz and about 400 KHz.

4. The system of claim 2 wherein said output gating means has a third input, said system further including selective overtone rejection means having an input connected to said band pass filter means and an output connected to said third input of said output gating means, said selective overtone rejection means being constructed to process signals received at its input to provide a signal at its output only when the amplitude peak of that part of the voltage signal burst above a predetermined frequency exceeds a predetermined percentage of the amplitude peak of that part of the signal burst that does not exceed that predetermined frequency, and said output gating means being constructed to provide said pulse at its output only during the time that said output gating means is provided at its third input the signal from said selective overtone rejection means.

5. The system of claim 4 wherein said selective overtone rejection means comprises:
- low-pass filter, having an output and an input that is connected to said output of said band pass filter means, said low-pass filter being constructed to pass frequencies up to 250 KHz;
- a high-pass filter having an output and an input that is connected to said output of said band pass filter means, said high-pass filter being constructed to pass frequencies of at least 250 KHz;
- first detector and filter means having an output and an input that is connected to said output of said low-pass filter, said first detector and filter means being constructed to provide a DC signal based on the maximum amplitude of the AC signal passed by said low-pass filter means from a signal burst;
- second detector and filter means having an output and an input that is connected to said output of said high-pass filter, said first detector and filter means being constructed to provide a DC signal based on the maximum amplitude of the AC signal passed by said high-pass filter means from a signal burst; and
- ccomparator means having first and second inputs connected to said outputs of said first and second detector and filter means, respectively, and having said output connected to said third input of said output gating means, said selective overtone rejection means being constructed so that, the DC voltage signal provided to said second input of said comparator means from said second detector and filter means is greater than a predetermined percentage of the DC voltage signal provided to said first input of said comparator means from said first detector and filter means to provide the signal from the output of said comparator means if the maximum amplitude of the high frequency content of the signal burst is greater than a predetermined percentage of the maximum amplitude of the low frequency content of the signal burst.

6. The system of claim 5 wherein said band pass filter means passes frequencies only of about 100 KHz and about 400 KHz.

7. The system of claim 4 and further including the receiver transducer means having its output connected to said input of said amplifier means.

8. The system of claim 7 wherein said band pass filter means passes frequencies only between about 100 KHz and about 400 KHz.

9. The system of claim 8 wherein said selective overtone rejection means comprises:
- a low-pass filter, having an output and an input that is connected to said output of said band pass filter means, said low-pass filter being constructed to pass frequencies up to 250 KHz;
- a high-pass filter having an output and an input that is connected to said output of said band pass filter means, said high-pass filter being constructed to pass frequencies of at least 250 KHz;
- said detector and filter means having an output and an input that is connected to said output of said low-pass filter, said first detector and filter means being constructed to provide a DC signal based on the maximum amplitude of the AC signal passed by said low-pass filter means from a signal burst;
- second detector and filter means having an output and an input that is connected to said output of said high-pass filter, said first detector and filter means being constructed to provide a DC signal based on the maximum amplitude of the AC signal passed by said high-pass filter means from a signal burst; and
- comparator means having first and second inputs connected to said outputs of said first and second detector and filter means, respectively, and having said output connected to said third input of said output gating means,
- said selective overtone rejection means being constructed so that, the DC voltage signal provided to said second input of said comparator means from said second detector and filter means is greater than a predetermined percentage of the DC voltage signal provided to said first input of said comparator means from said first detector and filter means to provide the signal from the output of said comparator means, if the maximum amplitude of the high frequency content of the signal burst is greater than a predetermined percentage of the maximum amplitude of the low frequency content of the same signal burst.

10. The system of claim 1 and further including the receiver transducer means having its output connected to said input of said amplifier means.

11. The system of claim 10 wherein said receiver transducer is a piezoelectric transducer, and said first and second outputs of said binary counter of said ring-down counter means provide a signal when the decimal count exceeds 100 and 1000, respectively, said system further including band pass filter means having an input connected to said output of said amplifier means and having an output connected to said input of said ring-down counter means to provide amplified signal bursts from said amplifier means to said ring-down counter means, said band pass filter means being constructed to pass frequencies between about 100 KHz and about 550 KHz.

12. The system of claim 11 wherein said band pass filter means passes frequencies only between about 100 KHz and about 400 KHz.

* * * * *